(12) United States Patent
Saleh

(10) Patent No.: US 8,653,702 B2
(45) Date of Patent: Feb. 18, 2014

(54) HANDS-FREE LIGHT CONTROLLER FOR HEADGEAR MOUNTED ILLUMINATION DEVICE

(76) Inventor: Hady Saleh, West Chester, OH (US)

( * ) Notice: Subject to any disclaimer, the term of this patent is extended or adjusted under 35 U.S.C. 154(b) by 510 days.

(21) Appl. No.: 13/048,993

(22) Filed: Mar. 16, 2011

(65) Prior Publication Data

US 2011/0227509 A1    Sep. 22, 2011

Related U.S. Application Data

(60) Provisional application No. 61/314,912, filed on Mar. 17, 2010.

(51) Int. Cl.
*H01H 35/00* (2006.01)
(52) U.S. Cl.
USPC ............................................. 307/116; 307/125
(58) Field of Classification Search
USPC ................................................... 307/116, 125
See application file for complete search history.

(56) References Cited

U.S. PATENT DOCUMENTS

| | | | |
|---|---|---|---|
| 2,541,042 A | 2/1951 | Curtis | |
| 3,229,059 A | 1/1966 | Beatty | |
| 3,586,798 A | 6/1971 | Holmes | |
| 3,683,168 A | 8/1972 | Tatje | |
| 4,462,064 A | 7/1984 | Schweitzer | |
| 4,975,937 A | 12/1990 | Horton et al. | |
| 5,101,504 A | 3/1992 | Lenz | |
| 5,329,637 A | 7/1994 | Walker | |
| 5,637,863 A | 6/1997 | Sanborn et al. | |
| 5,667,291 A | 9/1997 | Caplan et al. | |
| 5,850,613 A | 12/1998 | Bullecks | |
| 6,575,588 B2 | 6/2003 | Strehl | |
| 6,896,389 B1 | 5/2005 | Paul | |
| 7,008,074 B1 | 3/2006 | Halm | |
| 7,128,434 B1 | 10/2006 | Nally et al. | |
| 7,370,991 B1 | 5/2008 | Ellis-Fant | |
| 7,490,949 B2 | 2/2009 | Medinis | |
| 7,497,585 B2 | 3/2009 | Yu | |
| 2003/0067769 A1 | 4/2003 | Gilpin | |

*Primary Examiner* — Robert L. Deberadinis
(74) *Attorney, Agent, or Firm* — Thomas E. Lees, LLC

(57) ABSTRACT

A control device is provided, for controlling the supply of power from a remote power source to a headgear mounted illumination device to selectively turn the corresponding illumination source on and off. The control device includes an attachment feature that facilitates donning the control device on the body of a user. To operate the control device, the wearer causes hands-free, tactile contact with a switch contact surface of the control device, e.g., by bumping, pressing or otherwise engaging the switch contact surface against a limb or external structure.

20 Claims, 11 Drawing Sheets

HANDS-FREE LIGHT CONTROLLER FOR HEADGEAR MOUNTED ILLUMINATION DEVICE

CROSS REFERENCE TO RELATED APPLICATIONS

This application claims the benefit of U.S. Provisional Patent Application Ser. No. 61/314,912 filed Mar. 17, 2010, entitled "HANDS-FREE LIGHT CONTROLLER FOR HEADGEAR MOUNTED ILLUMINATION DEVICE", the disclosure of which is hereby incorporated by reference.

BACKGROUND

Various embodiments of the present invention relate in general, to headgear mounted illumination devices utilized by dental and medical professionals, jewelers, electronics technicians, etc., to provide illumination to an area of work, and more particularly, to controller devices that provide hands-free operation of the illumination source provided with such headgear mounted illumination devices.

In certain fields, particularly, dental and medical fields, it is sometimes necessary for a professional to illuminate an area of interest, e.g., to provide clear visibility of a selected part of a patient being worked on, examined or otherwise evaluated. Moreover, the professional often cannot be encumbered by the requirement to hold a light as both of the professional's hands may be required for carrying out a necessary task. Accordingly, the professional may utilize a headgear mounted illumination device that allows targeted positioning of light provided by the corresponding illumination source, e.g., based upon the orientation and positioning of the head of the professional.

BRIEF SUMMARY

According to various aspects of the present invention, a control device for controlling the supply of power from a remote power source to a headgear mounted illumination device, comprises a housing having a first major surface, a switch secured within the housing and a switch contact surface arranged with respect to the first major surface of the housing such that suitable tactile contact with the switch contact surface causes corresponding operation of the switch.

The switch has at least a first contact, a second contact and a switch element. A first electrical interconnect is electrically connected to the first contact of the switch and a second electrical interconnect is electrically connected to the second contact of the switch. Further, the first electrical interconnect has a terminal end having a coupler that electrically couples with a corresponding power input of the headgear mounted illumination device. Similarly, the second electrical interconnect has a terminal end having a coupler that electrically couples with the remote power source.

The control device also includes an attachment feature that facilitates donning the housing of the control device on the body of a user so as to position the control device for operation of the switch by the user, wherein the user operates the switch by causing hands-free, tactile contact with the switch contact surface to selectively make and break electrical continuity between the first electrical interconnect and the second electrical interconnect, thus turning the illumination source on the headgear mounted illumination device on and off at the discretion of the user in a hands-free manner.

According to further aspects of the present invention, a control device for controlling the supply of power from a remote power source to a headgear mounted illumination device comprises a housing having a first major surface. The housing contains a switch secured within the housing, a battery connector electrically connected in series with the switch, and a coupler electrically connected to the switch and battery connector. The switch has a switch element that is operable to transition the switch between open and closed states. The battery connector holds and electrically connects a battery, e.g., a battery comprised of at least one rechargeable battery cell, to the circuit within the housing. For instance, the battery connector may include at least a first terminal and a second terminal that form an electrical circuit with the switch and coupler.

The coupler is electrically connected to the switch and battery connector such that when a battery is installed in the battery connector, closing the switch makes electrical continuity from the battery to the coupler and opening the switch electrically breaks electrical continuity from the battery to the coupler. Additionally, the coupler connects a cable between the housing and the corresponding head mounted illumination source. The coupler may be implemented, for example, as a jack socket connected to the housing, which is configured to receive a jack of corresponding interconnecting cable.

A switch contact surface extends from the first major surface of the housing such that suitable tactile contact with the switch contact surface causes corresponding operation of the switch element. Additionally, an attachment feature is provided on the housing that facilitates donning the housing on the body of a user so as to position the control device for operation of the switch by the user, wherein the user operates the switch by causing hands-free, tactile contact with the switch contact surface to selectively make and break electrical continuity between the battery connector and the coupler, thus turning the illumination source of the headgear mounted illumination device on and off at the discretion of the user in a hands-free manner.

According to still further aspects of the present invention, a method of activating a headgear-mounted light in a sterile environment comprises wearing headgear including the mounted light, wearing a control device having a switch that electrically couples to the light of the headgear and bumping the switch without using hands, thus toggling the headgear-mounted light on and off. As described more fully herein, the control device includes a housing having a first major surface including an aperture there through, a switch within the housing including at least two positions for selectively controlling the light and a switch contact surface arranged with respect to the first major surface of the housing. The light is active when the switch is in a first position and the light is inactive when the switch is in a second position. To toggle the light, the switch contact surface is arranged with respect to the first major surface of the housing such that suitable tactile contact with the switch contact surface causes corresponding operation of the switch element. Accordingly, operation of the switch is controlled, for example, by bumping the switch without using hands to transition the switch position, thus toggling the headgear-mounted light on and off. For instance, the control device may be worn between the elbow and rib cage, around the waist, or other suitable location for tactile, bump contact using the user's elbow, hip, or other suitable, hands-free body part.

DETAILED DESCRIPTION

Figure 1:
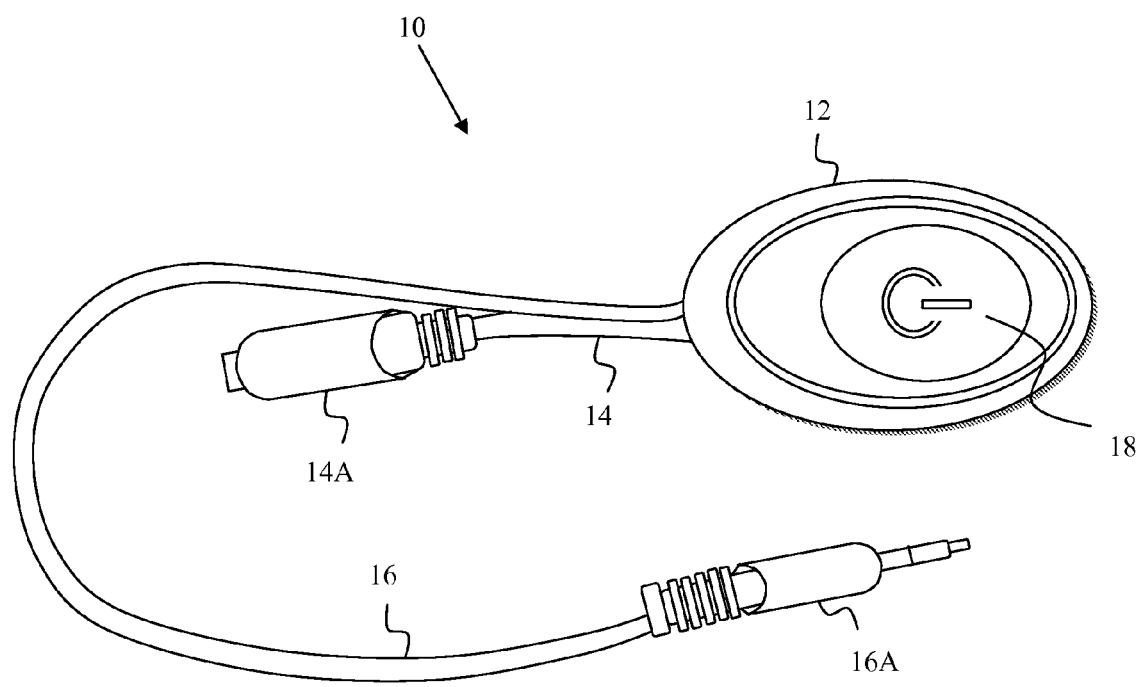
FIG. 1 is a front view of the control device according to various aspects of the present invention.

Referring now to the drawings, and in particular, to FIG. 1, a control device 10 is provided according to various aspects of the present invention. The control device 10 allows for hands-free, tactile operation of a switch to selectively energize and de-energize an illumination source in a headgear mounted illumination device, as will be described in greater detail herein. The control device 10 comprises a housing 12 that contains electronics including a switch. The control device 10 also comprises a first electrical interconnect 14 and a second electrical interconnect 16.

The first electrical interconnect 14 in the illustrative example, includes a first electrically conductive, flexible cable length that extends through and out of the housing 12. The first electrical interconnect 14 further terminates at a terminal end 14A, which includes a coupler that electrically couples the switch within the housing 12 to a corresponding power input of the headgear mounted illumination device when the control device 10 is suitably connected to the headgear mounted illumination device. In this regard, the coupler located at the terminal end 14A in the illustrative example is implemented as a socket. More particularly, the illustrated socket is a ⅛ inch (3.5 millimeter) socket, e.g., a female ⅛ stereo tip, ring, sleeve (TRS) mini-plug socket, having a molded socket enclosure that secures to the terminal end of the cable length. Alternatively, other coupler arrangements may be utilized, e.g., any complimentary, mating connectors, may be implemented for temporarily connecting and disconnecting the first electrical interconnect 14 of the control device 10 to the headgear mounted illumination device.

Correspondingly, the second electrical interconnect 16 in the illustrative example, includes a second electrically conductive, flexible cable length that extends through and out of the housing 12. The second electrical interconnect 16 further terminates at a terminal end 16A, which includes a coupler that electrically couples the switch within the housing 12 to a corresponding remote power source when the control device 10 is suitably connected to the remote power source. In this regard, the coupler located at the terminal end 16A in the illustrative example is implemented as a jack plug, e.g., a ⅛" (3.5 millimeter) stereo jack. Alternatively, other coupler arrangements may be utilized, e.g., any complimentary, mating connectors, may be implemented for temporarily connecting and disconnecting the second electrical interconnect 16 of the control device 10 to the power supply.

The control device 10 also includes a switch contact surface 18 arranged with respect to the housing 12 such that suitable tactile contact with the switch contact surface 18 causes corresponding operation of the switch contained within the housing 12. The illustrated switch contact surface 18 extends outward from the housing to provide a generally dome shaped extension from a major surface of the housing 12. As will be described in greater detail herein, the switch within the housing 12 is intended for hands-free operation thereof. As such, the switch contact surface 18 is sized and dimensioned to be suitable for hands-free operation. For example, the user may operate the switch by bump contact of the switch contact surface 18 with an elbow, hip, arm, leg or other body part of the user. Still further, the user may wear the control device 10 on their person, and bump the switch contact surface 18 to operate the switch with a structure external to the body of the user, e.g., by bumping the switch contact surface 18 on the edge of a work table, dental chair, etc. In this regard, the fingers of the user are not required to operate the switch.

Figure 2:
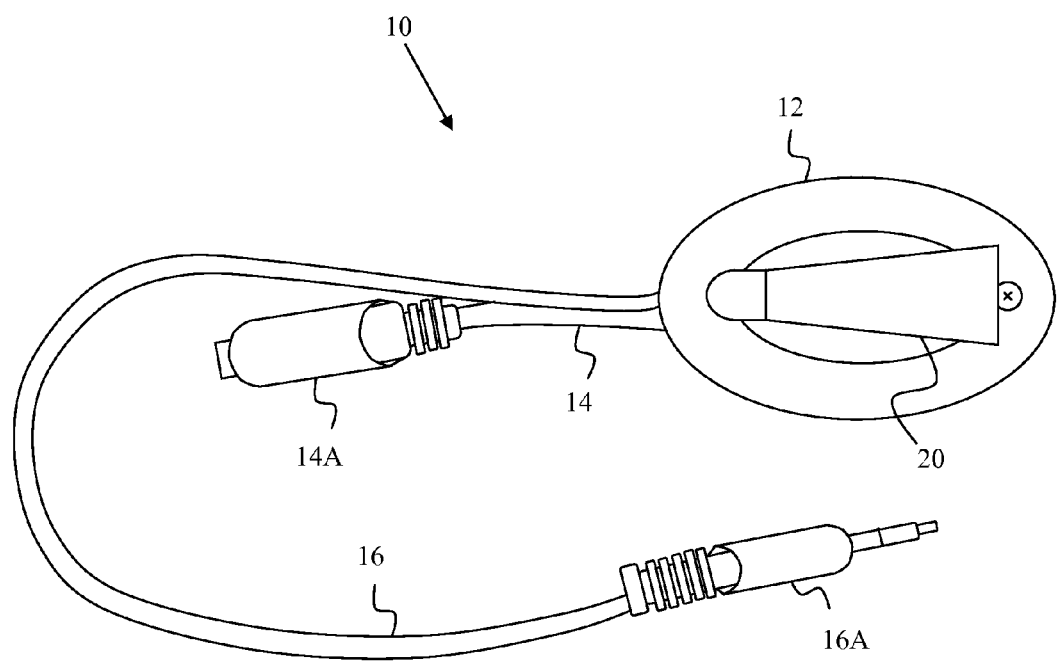
FIG. 2 is a bottom view of the control device according to various aspects of the present invention.
Figure 3:
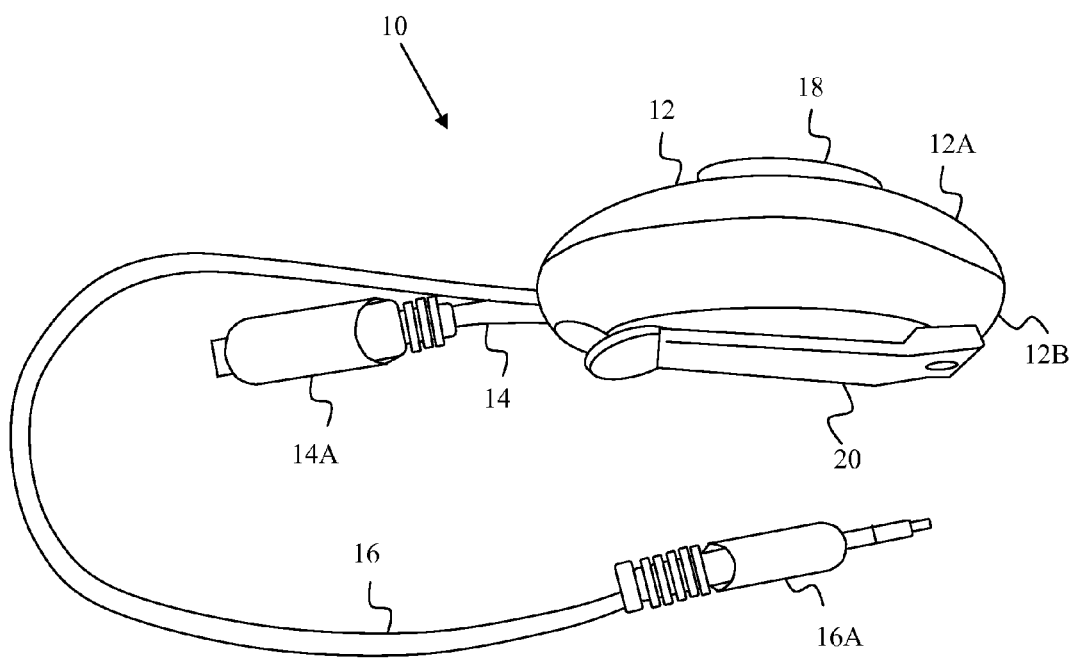
FIG. 3 is a side view of the control device according to various aspects of the present invention.

Referring to FIGS. 2 and 3, the control device 10 also includes an attachment feature 20. The attachment feature 20 facilitates donning and wearing the housing 12 of the control device 10 on the body of a user. For example, as illustrated, the attachment feature 20 includes a clip that can be attached to a belt, a pocket, gown or other article of clothing. The implementation of the attachment feature 20 as a clip is provided by way of illustration, and not by way of limitation. The attachment feature 20 may thus be implemented using other arrangements or configurations, e.g., so long as the housing 12 can be temporarily secured to the user in a manner that provides accessibility to the switch contact surface 18 for hands-free operation of the switch contained within the housing 12. As a few alternative and illustrative examples, the attachment feature 18 may be implemented as a pin, hook, loop, fastener, bracket, latch, buckle, spring biased jaws, Velcro® or other hook and loop fastener, magnets, etc.

Referring specifically to FIG. 3, the housing 12 may be implemented as a clam shell casing having a first clamshell section 12A and a second clamshell section 12B that mate together. In the illustrated implementation, the first clamshell section 12A has an aperture there through. The switch contact surface 18 extends across the aperture and also extends slightly outward from the surface of the first clamshell section 12A, as illustrated. For instance, the switch contact surface 18 may be implemented as a switch cover, e.g., a membrane that extends across the aperture and projects out from the aperture so as to provide an area that is actuated by hands-free bump contact. In this regard, the cover may be plastic, rubber or other suitable material. The switch contact surface 18 may also provide a seal, e.g., to protect the switch within the housing 12.

By way of illustration, the switch contact surface 18 can cover a significant portion of the top (i.e., major) surface of the housing for the control device 10, e.g., the first clamshell 12A as illustrated in FIG. 3A. For instance, the contact surface 18 can cover as much as approximately 25% or even greater surface area of the associated major surface. In other exemplary implementations, the contact surface 18 can cover as much as approximately 50% or even greater surface area of the associated major surface. Still further, in exemplary implementations, the contact surface 18 has a large diameter, e.g., greater than approximately 1" or more such that operation of the switch is suitable for hands-free operation. In this regard, the large, tactile contact surface 18 is not suitable for positioning on the side of a slim profile housing if finger operation is practically necessary to operate the switch. Moreover, the size of the contact surface 18 should not be so small that finger operation is practically necessary to operate the switch.

The second clamshell section 12B, opposite the first clamshell section 12A, includes a generally flattened surface portion for cooperation with the attachment feature 20, which is implemented as a clip in the illustrative example.

Figure 4:
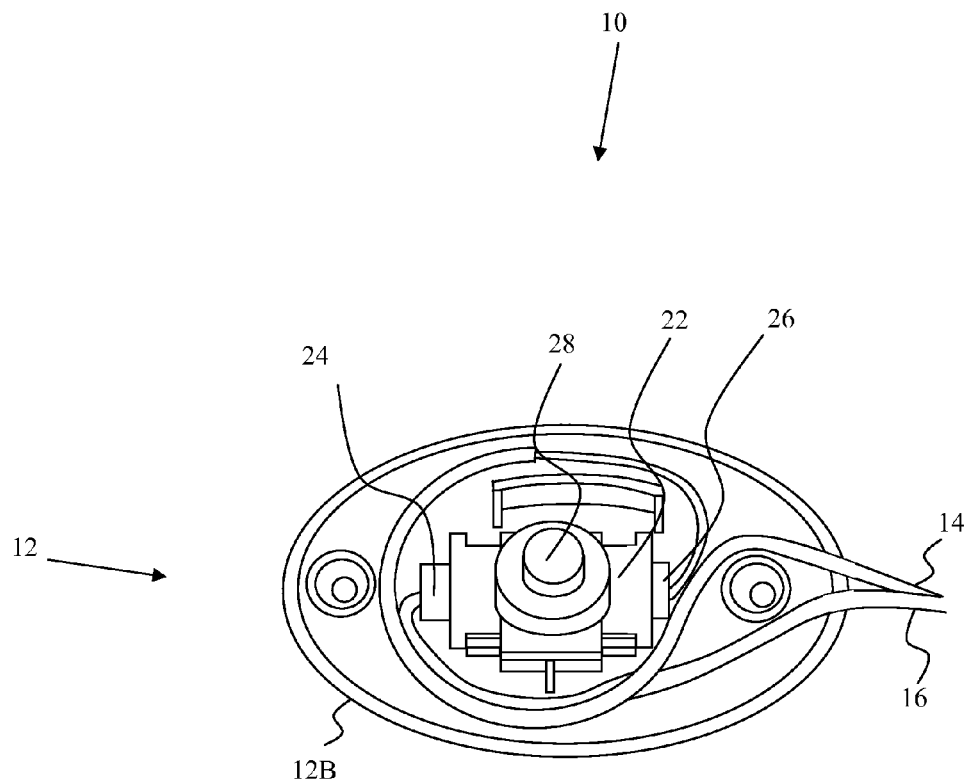
FIG. 4 is a top view of the control device with a portion of the housing removed to illustrate a switch according to various aspects of the present invention.

Referring to FIG. 4, electronics are included within the housing 12 for selectively coupling power from a remote power source to a headgear mounted illumination device. In an illustrative implementation, the electronics are implemented by a switch 22 secured within the housing 12. The switch 22, e.g., a mechanical, push button, latching switch, includes a first contact 24, a second contact 26 and a switch element 28. A conductor within the first electrical interconnect 14 is electrically connected to the first contact 24 of the switch 22. Correspondingly, a conductor within the second electrical interconnect 16 is electrically connected to the second contact 26 of the switch 22. As such, when the switch element 28 is toggled to an "ON" position, the first contact surface 24 is electrically shorted to the second contact surface 26, thus electrically connecting the conductor of the first electrical interconnect 14, which is connected to the first contact 24, to a corresponding conductor of the second electrical interconnect 16, which is connected to the second contact 26. Similarly, when the switch element 28 is toggled to an "off" position, the first contact surface 24 is electrically isolated from the second contact surface 26, thus breaking the electrical connection between the conductor of the first electrical interconnect 14, which is connected to the first contact 24, and the corresponding conductor of the second electrical interconnect 16, which is connected to the second contact 26.

In practice, the first electrical interconnect 14 and/or the second electrical interconnect 16 may carry one or more conductive wires. For instance, the headgear mounted illumination device may require direct current (DC) power in the range of 5-10 volts DC, to operate the corresponding illumination source. In this regard, the first electrical interconnect 14 and the second electrical interconnect 16 may each contain at least a first insulated wire that serves as a hot connection and a second wired that serves as a ground wire. Under this arrangement, the switch 22 may only be required to electrically make and break the connection between one of the two wires to control operation of the illumination source. However, the power and connection requirements of the headgear mounted illumination device will dictate the manner in which the switch 22 functions, and which wires define the most appropriate to switch between an open circuit and a closed circuit.

Figure 5:
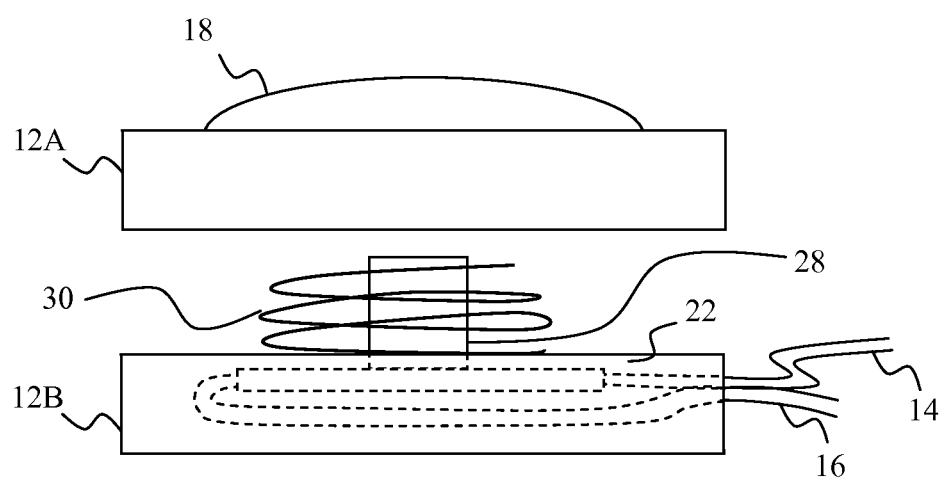
FIG. 5 is an assembly view of the control device according to various aspects of the present invention.

Referring to FIG. 5, when the housing is assembled, the switch element 28 is brought in register or is otherwise aligned with the switch contact surface 18. That is, the switch contact surface 18 is arranged with respect to the housing 12 such that suitable tactile contact with the switch contact surface 18 causes corresponding operation of the switch element 28 of the switch 22. In the illustrative example, a spring 30 is utilized to facilitate the interaction between the switch contact surface 18 and the switch element 28 of the switch 22.

The spring 30 may be utilized, for example, to supply a slight outward force to maintain the switch contact surface 18 in a suitable "ready" position. The spring 30 also helps to ensure that a predetermined amount of force is required to actuate the switch element 28 of the switch 22. Further, the spring 30 compresses as the switch contact surface 18 is depressed, which serves to reduce the likelihood of damage to the switch element 28, e.g., from an overly exerted force. In practice, other suitable arrangements may be implemented as an alternative to the spring 30.

Figure 6:
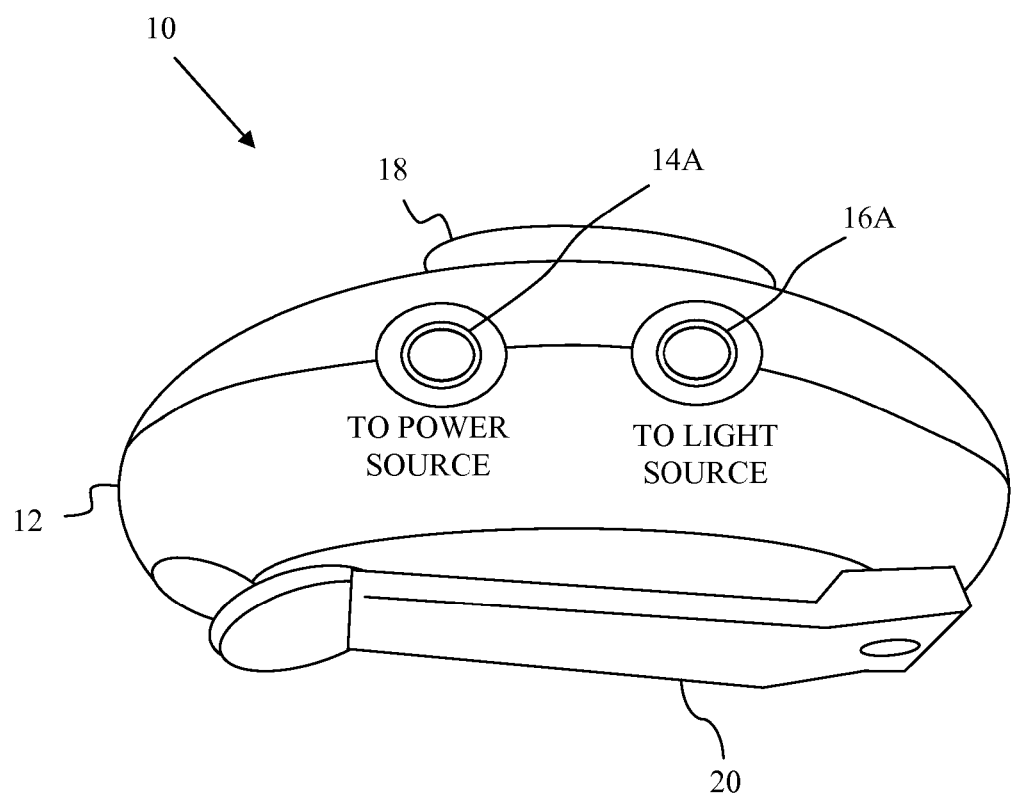
FIG. 6 is a side view illustrating a view of the control device according to further aspects of the present invention.

Referring to FIG. 6, according to further aspects of the present invention, the first electrical interconnect 14 may be contained within the housing 12. Under this arrangement, the coupler at the terminal end 14A of the electrical interconnect 14 may comprise a suitable socket mounted to the housing 12 that receives a corresponding jack plug of a connecting cable that electrically connects to the headgear mounted illumination device. Comparatively, as an alternative, as best illustrated in FIGS. 1-5, the first electrical interconnect 14 may also comprise an electrically conductive cable length that extends through and out of the housing 12, as described more fully herein. Moreover, the coupler at the terminal end 14A of the first electrical interconnect 14 may comprise a socket at the end of the cable length that receives the corresponding jack plug of a connecting cable that electrically connects to the headgear mounted illumination device. The terminal end 14A may also connect directly to the headgear mounted illumination device, e.g., using a suitable connecting adapter. Still further, although the coupler at the terminal end 14A is described with reference to a socket in the illustrative example of FIG. 6, other arrangements may alternatively be implemented, as described more fully herein.

With continued reference to FIG. 6, the second electrical interconnect 16 may also and/or alternatively be contained within the housing 12. In an analogous manner to that described above, the coupler terminal end 16A of the electrical interconnect 16 may comprise a suitable socket mounted to the housing 12 that receives a corresponding jack plug of a connecting cable that electrically connects to the remote power supply. Comparatively, as an alternative, as best illustrated in FIGS. 1-5, the second electrical interconnect 16 may also comprise an electrically conductive cable length that extends through and out of the housing 12, as described more fully herein. Moreover, the coupler at the terminal end 16A of the second electrical interconnect 16 may comprise a jack plug at the end of the cable length that plugs into a corresponding socket of a connecting cable that electrically connects to the remote power supply. The terminal end 16A may also connect directly to the remote power supply, e.g., by plugging directly into a battery pack, etc. For instance, the coupler at the terminal end 16A of the second electrical interconnect 16 may comprise a jack plug that plugs into a corresponding socket of the remote power supply battery pack. Still further, although the coupler at the terminal end 16A is described with reference to a jack plug, other arrangements may alternatively be implemented, as described more fully herein.

Figure 7:
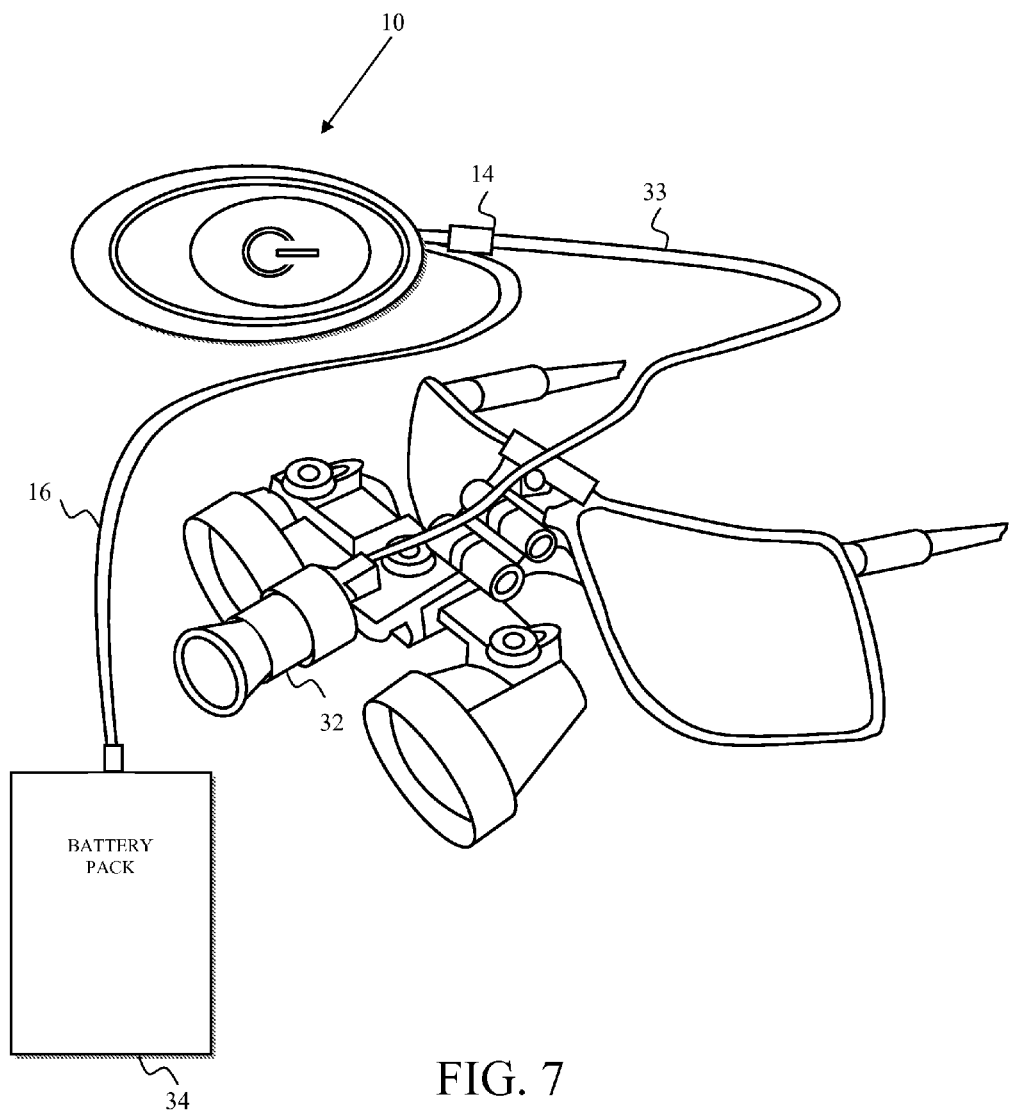
FIG. 7 is an illustration of the control device in cooperation with a corresponding headgear mounted illumination device and a power source according to various aspects of the present invention.

Referring to FIG. 7, the control device 10, e.g., as illustrated in FIG. 1, is schematically represented in a manner that interconnects a headgear mounted illumination device 32 to the control device 10 via the first electrical interconnect 14 and an additional connecting cable 33. The headgear mounted illumination device may comprise any illumination source for emitting light, such as a light emitting diode (LED) light, an incandescent light, xenon light, halide light or other light source that attaches to eyeglasses, a headband, a head-worn magnification loupe, face shield, binoculars or other head mounted instrument. A remote power source 34 connects to the control device 10 via the second electrical interconnection 16. In the exemplary arrangement, the second electrical interconnection 16 includes a coupler implemented as a jack plug that plugs directly into the remote power supply 34. In practice, other coupling arrangements may be implemented, e.g., depending upon the manner in which the couplers of the control device 10 are implemented, and/or depending upon the manner in which connections are made to the headgear mounted illumination source 32 and/or the remote power supply 34.

The remote power source 34 is typically implemented as a battery pack, e.g., a remotely located power pack that supplies the necessary power. However, it is also possible to implement the power source 34 as a room fixture, e.g., a power supply that plugs into an AC electrical outlet and provides power using a suitable connection cable. In this illustrative implementation, the user is tethered to the power source 34.

Figure 8:
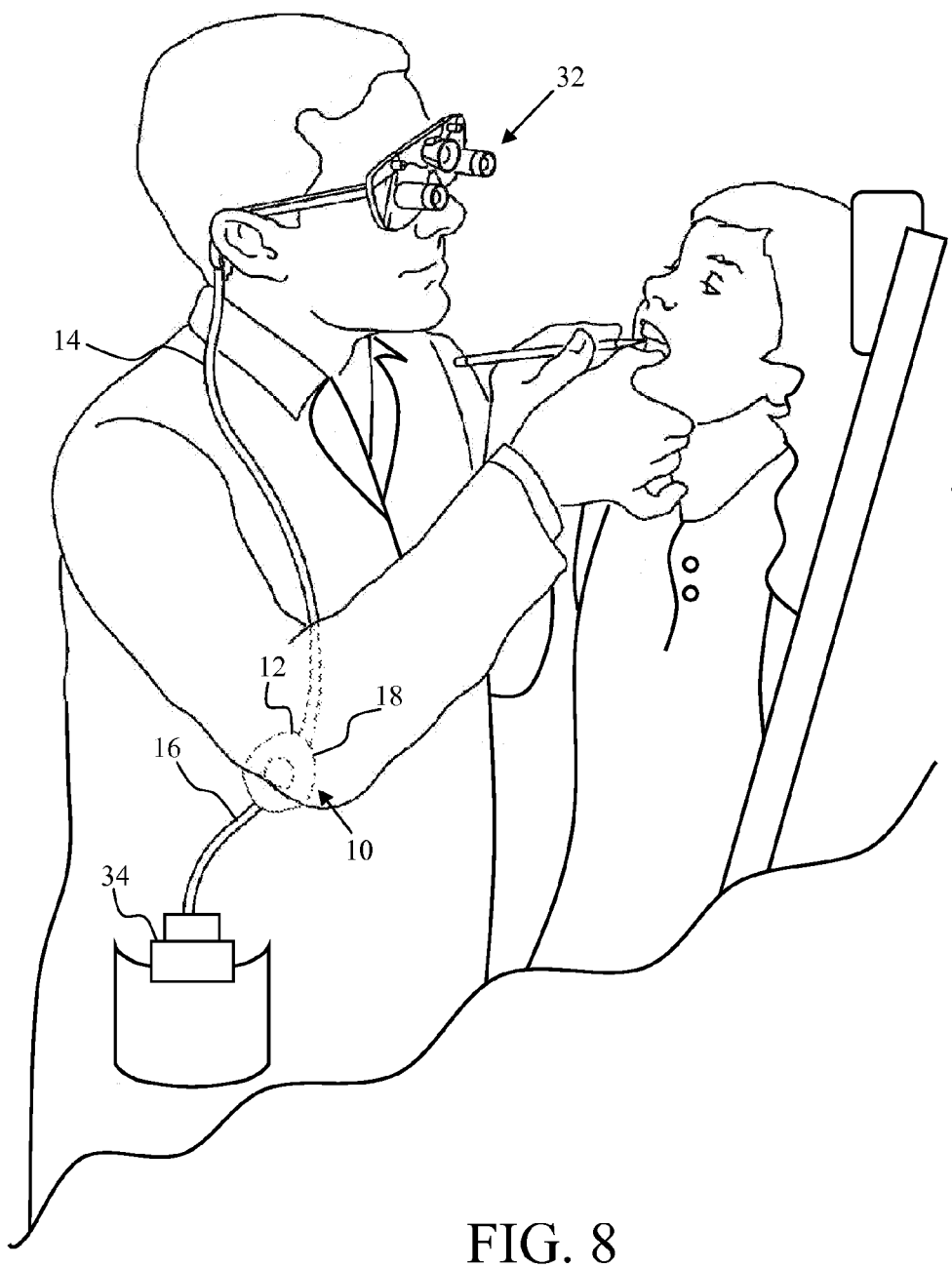
FIG. 8 is an illustration of the control device of FIG. 7 in an exemplary application according to various aspects of the present invention.

Referring to FIG. 8, it is essential in certain operations, e.g., dental and medical procedures, that the hands of a dentist, physician, surgeon, or other professional are free for manipulating various instruments. At the same time, it may be necessary to provide illumination to a specific work area in addition to the ambient illumination provided by the room upon which the work is being performed. For these purposes, headgear mounted illumination devices may be utilized. In practice, a dentist, physician or other user places the headgear mounted illumination device 32 upon their head, turns on the light and begins work.

However, there is also often a need for a dental or medical practitioner to maintain sterile hands during examination, surgery and other procedures. This makes it impractical for the user to control a conventional light source, e.g., by using a finger operated toggle switch to turn the light source on and off.

According to various aspects of the present invention, the headgear mounted illumination device 32 is coupled to the control device 10 by the first electrical interconnect 14 and an optional additional connecting cable if necessary. The control device 10 is further electrically coupled to a power source 34 using the second electrical interconnect 16 and an additional connecting cable if necessary.

In a medical or dental environment, the control device 10, according to various aspects of the present invention, allows a practitioner to operate a headgear mounted illumination device 32 at will by turning the illumination source on and off without jeopardizing manual sterility, and without requiring replacement and/or sterilization of the touched components between patients.

Rather, the control device 10 is donned by the user and is positioned for hands-free operation. For instance, the attachment feature 20, such as a clip, facilitates donning the housing 12 of the control device 10 on the body of a user so as to position the switch for hand-free, tactile operation. Moreover, as described more fully herein, the switch contact surface 18 has a wide engagement surface that enables the switch 22 donned by a user, to be easily actuated, e.g., by bump contact. Thus, the control device 10 may be positioned on the body of the user such that the user can practice hands-free engagement with the switch contact surface 18 to selectively make and break electrical continuity between the power source 34 and the headgear mounted illumination device 32, thus providing a hands-free way of turning the light of the headgear mounted illumination source on and off.

By way of example, the control device 10 may be clipped or otherwise secured to a lab coat, surgical gown, or other garment at a position suitable for hands-free operation. In the illustrative example, the remote power source 32 is located in the pocket of a lab coat. The control device 10 is clipped to the lab coat proximate to an arm or elbow portion of the lab coat. As such, the user may operate the switch of the control device 10 by bumping, pushing or otherwise pressing against the switch contact surface 18, such as with an elbow or arm member positioned proximate to the control device 10 to selectively turn the light on and off. This operation can be performed as frequently as desired without jeopardizing manual sterility.

As yet another illustrative example, the control device 10 may be clipped to a belt or otherwise positioned on the user such that the switch contact surface 18 can be bumped to turn the switch on and off without requiring contact of the hands, e.g., by using a hip, elbow, leg or other body feature or limb, or by using a structure within the environment, e.g., by bumping the switch contact surface 18 against a dental chair, table, etc. As yet additional examples, the control device 10 may clip onto the inside or outside of surgical scrubs or other body location. This avoids the need to touch the switch with the hands of the user, thus for example, avoiding contaminating a sterilized environment.

As yet further exemplary illustrations, the attachment feature 20 of the controller 10 may further comprise a clasp, hook, clip, lanyard or other suitable structure that allows the device to be suitable positioned for hands-free operation. Often, the implementation of the attachment feature 20 will dictate how the control device 10 is donned by the user. Regardless, the attachment feature 20 facilitates donning the control device 10 on the body of a user so as to position the control device 10 for operation of the switch 22 by the user by causing hands-free, tactile contact with the switch contact surface 18. As noted in greater detail herein, tactile contact with the switch contract surface 18 causes the control device 10 to selectively make and break electrical continuity between at least one conductor of the first electrical interconnect 14 and at least one corresponding conductor of the second electrical interconnect 16, thus turning the illumination source on the headgear mounted illumination device on and off at the discretion of the user in a hands-free manner.

In an exemplary operation, the control device 10 is inserted, e.g., in series, between the headgear mounted illumination device 32 and the remote power source 34 such that operation of the control device 10 selectively turns the illumination source of the headgear mounted illumination device on and off, e.g., by selectively controlling the delivery of power from the remote power supply 34 to the headgear mounted illumination device 32.

In certain applications, it is advantageous for the user of a headgear mounted illumination device 32 to turn the illumination source on and off multiple times during the course of completing a task. For instance, a dentist may need a light source to illuminate a work area in the mouth of a patient. However, the dentist may further wish to refrain from working periodically to stop and talk with the patient, e.g., to ask questions, explain procedures etc. However, when the dentist refocuses attention from the work area to the patient, the dentist is likely to look towards the face of the patient, thus shining a bright light directly into the eyes and face of the patient. This can be distracting and annoying to the patient. Moreover, the dentist may require a sterile environment. As such, in conventional practice, the dentist may withhold turning the light off to prevent contamination of the work area.

However, according to various aspects of the present invention, the dentist may bump contact the switch of the control device 10 to quickly turn the illumination source off while the light is not necessary, then quickly and easily re-engage the light to return to working Still further, the dentist can turn the illumination source of the headgear mounted illumination device 32 off when its light is not necessary, thus conserving battery life of the product, without requiring hand contact with a control switch on the remote power supply, thus preserving a sterile environment.

In view of the above, a method of activating a headgear-mounted light in a sterile environment comprises wearing headgear including the mounted light, and wearing a control device that electrically couples to the light of the headgear. As described more fully herein, the control device includes a housing having a first major surface including an aperture there through, a switch within the housing including at least two positions for selectively controlling the light and a switch contact surface arranged with respect to the first major surface of the housing. The light is active when the switch is in a first position and the light is inactive when the switch is in a second position. To toggle the light, the switch contact surface is arranged with respect to the first major surface of the housing such that suitable tactile contact with the switch contact surface causes corresponding operation of the switch element. Accordingly, operation of the switch is controlled, for example, by bumping the switch without using hands to transition the switch position, thus toggling the headgear-mounted light on and off. For instance, the control device may be worn between the elbow and rib cage, around the waist, or other suitable location for tactile, bump contact using the user's elbow, hip, or other suitable, hands-free body part.

Figure 9:
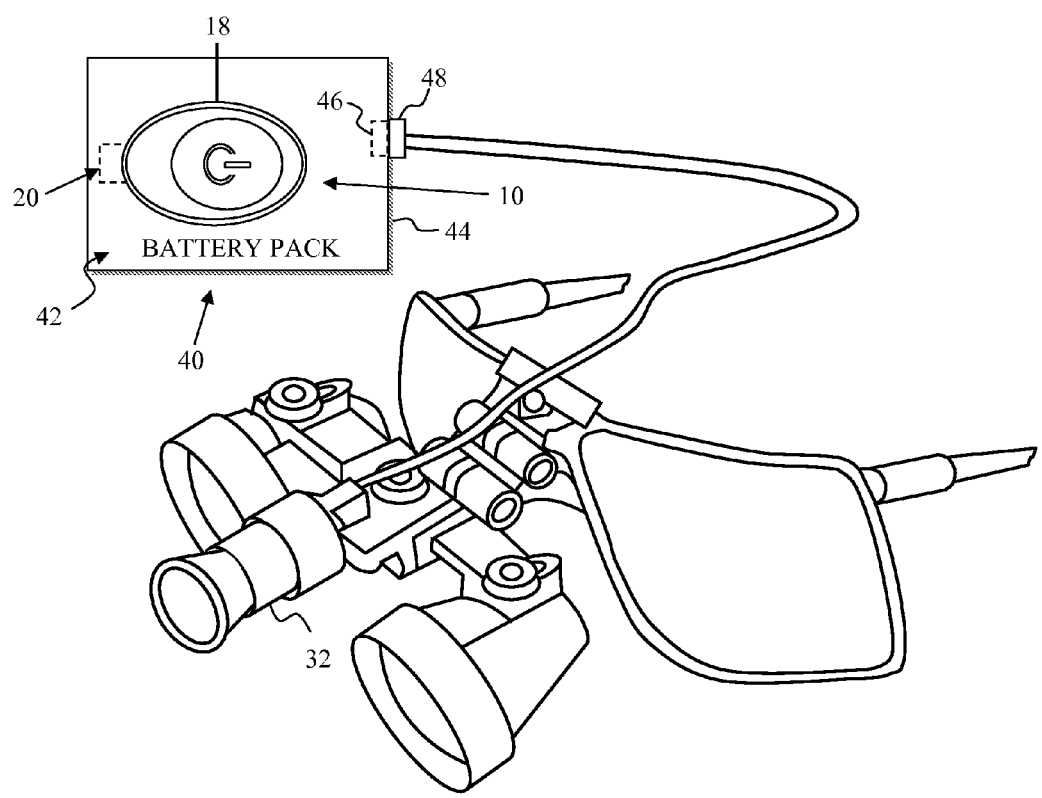
FIG. 9 is an illustration of the control device in cooperation with a corresponding headgear mounted illumination device and a power source where the control device is integrated onto a surface of the power source, according to various aspects of the present invention.

Referring to FIG. 9, a control device 10 is illustrated for controlling the supply of power from a remote power source to a headgear mounted illumination device according to further aspects of the present invention. The control device 10 is illustrated in a manner that only requires a single electrical interconnect to couple a headgear mounted illumination device 32 to the control device 10. In this illustrative example, the control device 10 comprises a hands-free tactile switch that is integrated with a remote power source 34. More particularly, the remote power source 34 may comprise a battery power pack that is packaged in a housing sized to be clipped, attached or otherwise worn by the user.

As illustrated, the remote power source and control device are packaged in a housing 40 having a first major surface 42 that defines an outer face of the housing 40. The housing 40 also includes a second major surface that is opposite the first major surface 42. The second major surface may include an attachment feature 20 analogous to the attachment feature described more fully herein. The attachment feature 20 is illustrated in dashed lines to indicate that that second major surface is generally parallel to, and spaced from the first major surface by an edge surface 44 of the housing 40.

The edge surface 44 is generally thin in profile. In the illustrative exemplary housing 40, a coupler 46 is located about a top portion of the edge surface 44. The coupler 46 may be implemented for example, as a jack socket that receives or otherwise mates with a corresponding jack 48 of a cable, e.g., interconnect 50 that further connects to the headgear mounted illumination source 32. In an analogous manner to that described more fully herein, the coupler 46 may be implemented in any number of configurations. Moreover, the coupler 46 can be relocated to end of a cable that extends from the housing 40, e.g., to plug into or otherwise couple with the headgear mounted illumination source 32. In this regard, the interconnection cable may be hardwired to the electronics, switch and battery in the housing 40 and thus extend through the housing 40, e.g., through the top portion of the edge surface 44.

A switch contact surface 18 analogous to the switch contact surface set out more fully herein, is integrated with the first major surface 42 of the housing 40. More particularly, the switch contact surface 18 extends from the first major surface of the housing 40 such that suitable tactile contact with the switch contact surface 18 causes corresponding operation of a switch element of a switch within the housing, in a manner that is analogous to that described more fully herein. In this regard, the first major surface 42 is dimensioned so as to accommodate the switch contact surface 18.

Figure 10:
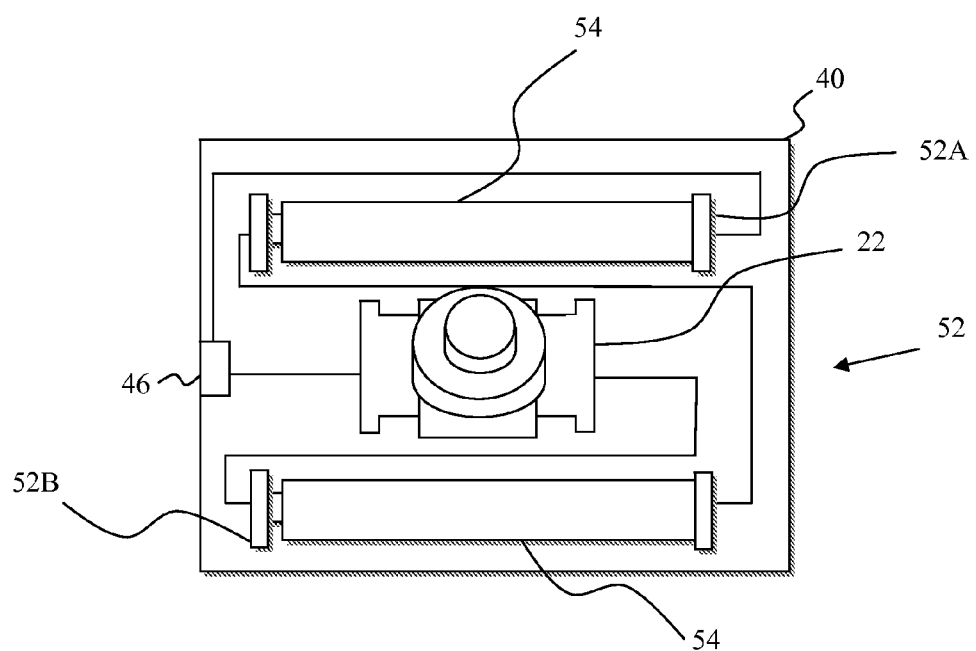
FIG. 10 is a schematic illustration of exemplary internal components of the control device of FIG. 9, according to various aspects of the present invention.

Referring to FIG. 10 a switch 22 is secured within the housing 40. As noted above, the switch 22 includes a switch element that is operable to selectively turn on and off a headgear mounted illumination source. The housing 40 also includes the electronics, wiring and connections necessary to power the associated illumination source 32. For instance, as illustrated, the housing 40 includes the coupler 46, e.g., implemented for example, as a jack socket and a battery connector 52. The coupler 46 is configured to connect a cable between the housing 40 and the corresponding head mounted illumination source.

The battery connector 52 is electrically connected in series with the switch 22 and is provided for holding and electrically connecting a battery to the circuit within the housing 40. More particularly, the battery connector 48 is provided to enable a battery comprised of at least one battery cell, e.g., a rechargeable battery cell, to be placed in an electrical circuit within the housing 40. In this regard, the battery connector 48 is electrically connected in series with the switch 22. For purposes of illustration, two batteries 54 are shown installed in housing and are electrically coupled to the battery connector 52, although other arrangements may be implemented.

The coupler 46 is connected to the switch 22 and the battery connector 52 such that when a battery is installed in the battery connector 52, closing the switch 22 makes electrical continuity from the battery to the coupler 46 and opening the switch 22 electrically breaks electrical continuity from the battery to the coupler. In an illustrative example, closing the switch 22 couples a voltage from the battery to the coupler 46 and opening the switch 22 electrically isolates voltage from the battery to the coupler 46.

More particularly, in the illustrative example, a first connection of the coupler 46 is coupled to a terminal 52A of the battery connector 52. A second terminal 52B of the battery connector 52 couples to a first contact of the switch 22, and a second contact of the switch 22 couples to a second contact of the coupler 46. As illustrated, the battery connector 52 includes connections necessary to connect two rechargeable battery cells 54 in series. However, the circuitry, including the illustrated battery cells, is presented by way of illustration and not by way of limitation. Other circuitry and/or alternative features may also be implemented. Moreover, the battery of the power source may be implemented by one or more battery cells. In this regard, the type and number of batteries will likely determine the specific implementation and structural configuration of the battery connector 52.

Referring to FIGS. 9 and 10, the attachment feature 20 facilitates donning the housing 40 on the body of a user so as to position the control device for operation of the switch 22 by the user, wherein the user operates the switch by causing hands-free, tactile contact with the switch contact surface 18 to selectively make and break electrical continuity between the battery connector 52 and the coupler 46, thus turning the illumination source of the headgear mounted illumination device on and off at the discretion of the user in a hands-free manner. For instance, the attachment feature 20 may comprise a clip or other fastening arrangement to secure the housing 40 to a belt, belt loop or other garment worn by the user as described more fully herein.

Figure 11:
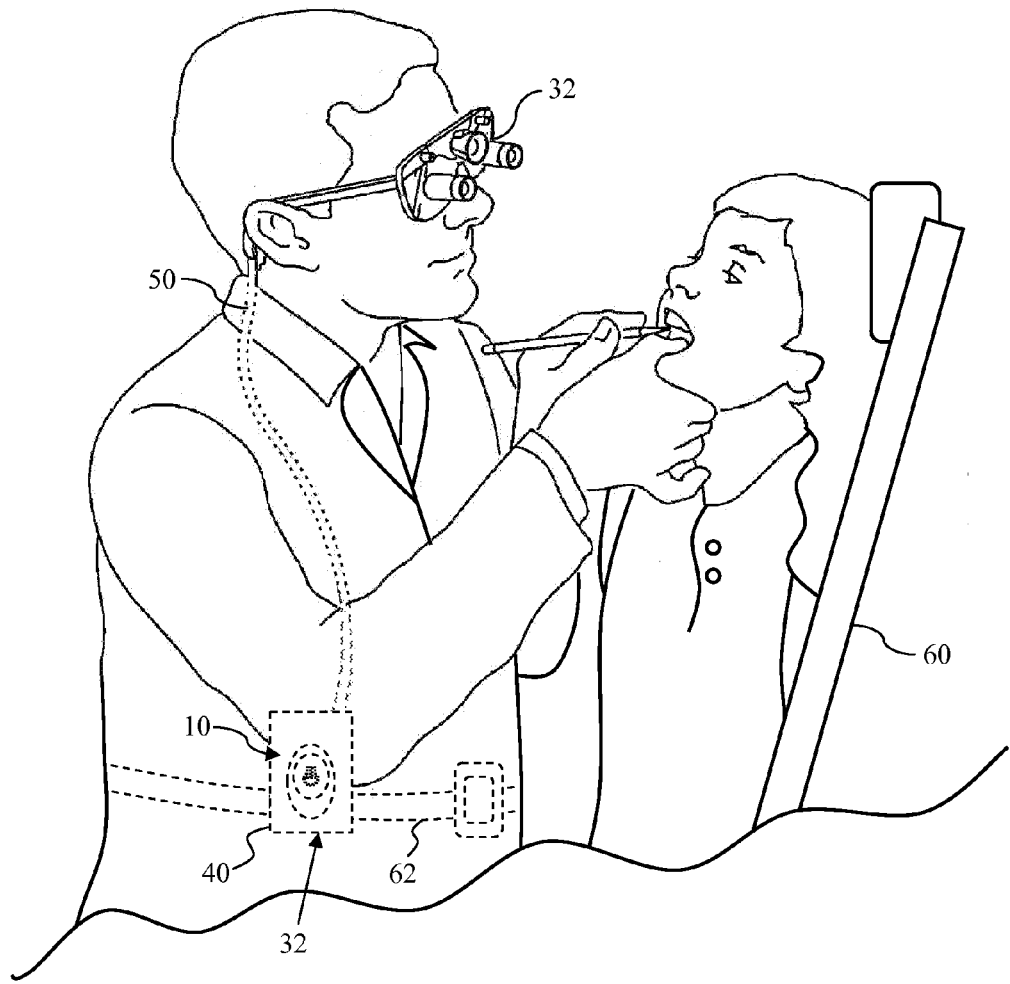
FIG. 11 is an illustration of the control device of FIG. 9 in an exemplary application according to various aspects of the present invention.

Referring to FIG. 11, as noted above, it is essential in certain operations, e.g., dental and medical procedures, that the hands of a dentist, physician, surgeon, or other professional are free for manipulating various instruments. At the same time, it may be necessary to provide illumination to a specific work area in addition to the ambient illumination provided by the room upon which the work is being performed. Moreover, as an illustrative example, a dentist may be seated while work is being performed. For instance, the dentist may be examining a person seated in a dental chair 60.

Moreover, as noted above, there is also often a need for a dental or medical practitioner to maintain sterile hands during examination, surgery and other procedures. This makes it impractical for the dentist to control a conventional light source as conventional power packs provide a finger operated toggle switch to turn the light source on and off. Thus, touching the switch will cause potential contamination.

However, according to various aspects of the present invention, the headgear mounted illumination device 32 is coupled to the control device 10 integrated into the housing 40 of the power source 34, e.g., a battery power pack by an electrical interconnect 50. The housing 40 also includes the electronics of the power source 34, e.g., batteries, etc. As such, the wiring between the control device 10 and the power source 34 are carried out within the housing 40. Moreover, the housing 40 may be donned by clipping the housing 40 to a belt 62, belt loop or other article of clothing. This allows the dentist to wear a lab coat, gown or other garment over the housing 40 and corresponding interconnect 50 so that only a single wire is run neatly under garments and out of the way, thus promoting a sterile environment.

In this regard, due to positioning of the contact surface 18 of the switch on the first major surface of the housing 40, the switch is positioned to generally avoid unintended contact with a force sufficient to trigger the switching device. Still further, the size and the predetermined pressure required to bump, press or otherwise push and actuate the contact surface 18 make intended hands-free actuation of the switch easy for the user, even through one or more layers of clothing. For instance, as illustrated, the dentist, while sitting down, has an elbow positioned within easy reach of a hip position where the housing 40 is donned. This makes frequent operation of the switch possible, even through a gown, lab coat and/or other articles of clothing, without requiring large, awkward limb movements, and does not require the use of fingers that would otherwise become contaminated by contact with a light switching device.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description herein has been presented for purposes of illustration and description, but is not intended to be exhaustive or limited to the invention in the form disclosed. Many modifications and variations will be apparent to those of ordinary skill in the art without departing from the scope and spirit of the invention.

Having thus described the invention of the present application in detail and by reference to embodiments thereof, it will be apparent that modifications and variations are possible without departing from the scope of the invention defined in the appended claims.

What is claimed is:

1. A control device for controlling the supply of power from a remote power source to a headgear mounted illumination device, comprising:
a housing having a first major surface;
a switch secured within the housing, the switch having at least a first contact, a second contact and a switch element;
a switch contact surface arranged with respect to the first major surface of the housing such that suitable tactile contact with the switch contact surface causes corresponding operation of the switch element;
a first electrical interconnect electrically connected to the first contact of the switch, the first electrical interconnect having a terminal end having a coupler that electrically couples the first contact of the switch to a corresponding power input of the headgear mounted illumination device;
a second electrical interconnect electrically connected to the second contact of the switch, the second electrical interconnect having a terminal end having a coupler that electrically couples the second contact of the switch to the remote power source; and
an attachment feature that facilitates donning the control device on the body of a user so as to position the control device for operation of the switch by the user wherein the user operates the switch by causing hands-free, tactile contact with the switch contact surface to selectively make and break electrical continuity between the first electrical interconnect and the second electrical interconnect, thus turning the illumination source on the headgear mounted illumination device on and off at the discretion of the user in a hands-free manner.

2. The control device according to claim 1, wherein:
the housing comprises a clamshell casing having a first clamshell section including the first major surface that mates with a second clamshell section, the first major surface having an aperture there through; and
the switch contact surface comprises a cover extending across the aperture and extending out from the aperture so as to provide an area that is actuated by hands-free bump contact.

3. The control device according to claim 2, wherein:
the switch contact surface comprises a surface area of at least 25% of the first major surface; and
the switch comprises a mechanical push button latching switch.

4. The control device according to claim 1, wherein:
the coupler at the terminal end of the first electrical interconnect comprises a socket mounted to the housing that receives a corresponding jack plug of a connecting cable that electrically connects to the headgear mounted illumination device.

5. The control device according to claim 1, wherein:
the first electrical interconnect comprises an electrically conductive cable length that extends through and out of the housing; and
the coupler at the terminal end of the first electrical interconnect comprises a socket at the end of the cable length that receives a corresponding jack plug of a connecting cable that electrically connects to the headgear mounted illumination device.

6. The control device according to claim 1, wherein:
the coupler at the terminal end of the second electrical interconnect comprises a socket mounted to the housing that receives a corresponding jack plug of a connecting cable that electrically connects to the remote power supply.

7. The control device according to claim 1, wherein:
the second electrical interconnect comprises an electrically conductive cable length that extends through and out of the housing; and
the coupler at the terminal end of the second electrical interconnect comprises a jack plug at the end of the cable length that plugs into a corresponding socket of a connecting cable that electrically connects to the remote power supply.

8. The control device according to claim 1, wherein:
the attachment feature comprises a clip that facilitates donning the housing of the control device by temporarily securing the housing to an article of clothing worn by the user.

9. A control device for controlling the supply of power from a remote power source to a headgear mounted illumination device, comprising:
a housing having a first major surface;
a switch secured within the housing, the switch having a switch element;
a switch contact surface extending from the first major surface of the housing such that suitable tactile contact with the switch contact surface causes corresponding operation of the switch element;
a battery connector within the housing that is electrically connected in series with the switch, the battery connector for holding a battery;
a coupler electrically connected to the switch and battery connector such that when a battery is installed in the battery connector, closing the switch makes electrical continuity from the battery to the coupler and opening the switch electrically breaks electrical continuity from the battery to the coupler, the coupler configured to connect a cable between the housing and the corresponding head mounted illumination source; and
an attachment feature that facilitates donning the housing on the body of a user so as to position the control device for operation of the switch by the user, wherein the user operates the switch by causing hands-free, tactile contact with the switch contact surface to selectively make and break electrical continuity between the battery connector and the coupler, thus turning the illumination source of the headgear mounted illumination device on and off at the discretion of the user in a hands-free manner.

10. The control device according to claim 9, wherein:
the housing comprises a clamshell casing having a first clamshell section including the first major surface that mates with a second clamshell section, the first major surface having an aperture there through; and
the switch contact surface comprises a cover extending across the aperture and extending out from the aperture so as to provide an area that is actuated by hands-free bump contact.

11. The control device according to claim 10, wherein:
the switch contact surface comprises a surface area of at least 25% of the first major surface; and
the switch comprises a mechanical push button latching switch.

12. The control device according to claim 9, wherein the coupler comprises a jack socket configured to receive a jack of a cable to couple the housing to the head mounted illumination source.

13. The control device according to claim 9, wherein the attachment device comprises a belt clip positioned on a second major surface of the housing.

14. The control device according to claim 9, wherein the battery connector comprises at least a first terminal and a second terminal that form an electrical circuit with the switch and the coupler.

15. The control device according to claim 9, wherein closing the switch makes electrical continuity by coupling a voltage from the battery to the coupler and opening the switch breaks electrical continuity by electrically isolating a voltage from the battery to the coupler.

16. A method of activating a headgear-mounted light in a sterile environment, the method comprising:
wearing headgear including the mounted light;
wearing a control device that electrically couples to the light of the headgear, wherein the control device includes:
a housing having a first major surface including an aperture there through,
a switch within the housing including at least two positions for selectively controlling the light wherein the light is active when the switch is in a first position and the light is inactive when the switch is in a second position,
a switch contact surface arranged with respect to the first major surface of the housing such that suitable tactile contact with the switch contact surface causes corresponding operation of the switch element; and
bumping the switch without using hands to transition the switch position, thus toggling the headgear-mounted light on and off.

17. The method of claim 16, where within the step of wearing a device, the device further includes an integrated power supply electrically coupled to the light, wherein the switch allows power to flow from the power source to the light when the switch is in the first position and prevents power from flowing from the light to the power supply when the switch is in the second position.

18. The method of claim 16 further comprising the step of wearing a power supply that electrically couples to the light through the device, and wherein the switch allows power to flow from the power source to the light when the switch is in the first position and prevents power from flowing from the light to the power supply when the switch is in the second position.

19. The method of claim 16, where within the step of wearing a device, the switch contact surface further includes a cover extending across the aperture and extending out from the aperture so as to provide an area that is actuated by hands-free bump contact.

20. The method of claim 16, wherein the step of bumping the switch further includes bumping the switch using the user's elbow to transition the switch from the switch's current position to another position.

* * * * *